United States Patent [19]
Aquila et al.

[11] Patent Number: 6,013,843
[45] Date of Patent: Jan. 11, 2000

[54] CONTINUOUS INDUSTRIAL PRODUCTION OF UNSATURATED ALIPHATIC ALDEHYDES IN A TUBE BUNDLE REACTOR

[75] Inventors: Werner Aquila, Mannheim; Hartwig Fuchs, Ludwigshafen; Otto Wörz, Friedelsheim; Wilhelm Ruppel, Frankenthal; Klaus Halbritter, Heidelberg, all of Germany

[73] Assignee: BASF Aktiengeselllschaft, Ludwigshafen, Germany

[21] Appl. No.: 09/085,836

[22] Filed: May 28, 1998

[30] Foreign Application Priority Data

May 28, 1997 [DE] Germany .......................... 197 22 567

[51] Int. Cl.⁷ .................................................. C07C 45/00
[52] U.S. Cl. .......................... 568/473; 568/450; 568/471
[58] Field of Search ................................... 568/471, 450, 568/473

[56] References Cited

U.S. PATENT DOCUMENTS

| | | |
|---|---|---|
| 2,042,220 | 5/1936 | Groll et al. . |
| 3,284,170 | 11/1966 | Neely . |
| 3,778,477 | 12/1973 | Mueller et al. . |
| 3,894,916 | 7/1975 | Fischer et al. . |
| 4,094,535 | 6/1978 | Yang et al. . |
| 4,110,403 | 8/1978 | Ichikawa et al. . |
| 4,154,762 | 5/1979 | Huang et al. . |
| 4,165,342 | 8/1979 | Dudeck et al. . |
| 5,149,884 | 9/1992 | Brenner et al. . |

FOREIGN PATENT DOCUMENTS

| | | |
|---|---|---|
| 2 231 650 | 12/1974 | France . |
| 2 386 509 | 11/1978 | France . |
| 20 20 865 | 11/1971 | Germany . |
| 2 243 810 | 10/1973 | Germany . |
| 25 17 859 | 3/1976 | Germany . |
| 27 15 209 | 11/1978 | Germany . |

OTHER PUBLICATIONS

Derwent Abstracts, JP 60–246340, Dec. 06, 1985.
Derwent Abstracts, JP 58–059933, Sep. 04, 1983.

*Primary Examiner*—Paul J. Killos
*Assistant Examiner*—J. Parsa
*Attorney, Agent, or Firm*—Oblon, Spivak, McClelland, Maier & Neustadt, P.C.

[57] ABSTRACT

A process for continuous industrial production of unsaturated aliphatic aldehydes having a boiling range from 95 to 136° C. by oxidative dehydrogenation of the corresponding alcohols with an oxygen-comprising gas over a supported catalyst consisting of copper, silver and/or gold on an inert support in a tube bundle reactor, rapid cooling of the reaction gases and removal of the aldehydes from the resulting condensate with recycling of the unconverted alcohols comprises a) vaporizing the alcohol,
b) admixing the alcohol vapor with an oxygen-comprising gas,
c) initially passing the resulting oxygen-comprising alcohol vapor at above the dew point of the alcohol but below the commencement temperature of the reaction through a layer of one of the abovementioned supported catalysts which is at least 0.5 cm in thickness and only then
d) reacting the oxygen-comprising alcohol vapor at from 300 to 600° C. in a sufficient number, for the desired capacity, of parallel reaction tubes surrounded by a fluidic heat transfer medium, packed with the supported catalyst and having an internal diameter D of from about 0.5 to 3 cm and a length of at least 5 cm, to form the corresponding aldehyde.

10 Claims, 3 Drawing Sheets

CONTINUOUS INDUSTRIAL PRODUCTION OF UNSATURATED ALIPHATIC ALDEHYDES IN A TUBE BUNDLE REACTOR

FIELD OF THE INVENTION

The present invention relates to an improvement in the continuous industrial production of unsaturated aliphatic aldehydes by catalytic oxidative dehydrogenation of unsaturated aliphatic alcohols in a tube bundle reactor, especially to an improvement in the continuous production of 3-methyl-2-buten-1-al (prenal) from 3-methyl-2-buten-1-ol (prenol) and/or 3-methyl-3-buten-1-ol (isoprenol).

DESCRIPTION OF THE PRIOR ART

The problem with this reaction is that it is strongly exothermic, that the reaction rate depends strongly on the reaction temperature and that the reactants and also the products are extremely unstable.

U.S. Pat. No. 2,042,220 discloses oxidizing isoprenol with an excess of oxygen at 360 to 550° C. in the presence of metal catalysts, for example copper and silver catalysts, to form 3-methyl-3-buten-1-al (isoprenal). The catalysts can be alloys, metal compounds or elemental metal. Activated catalysts are preferred; activating options are said to include surface amalgamation of the metal and subsequent heating of the metal surface. In the Examples, copper and silver catalysts are prepared by reducing copper oxide particles under hydrogen at 300° C. or by amalgamation and heating of silver wire networks. According to DE-B-20 41 976, the process of U.S. Pat. No. 2,042,220 by-produces appreciable amounts of undesirable by-products.

DE-A-25 17 859 describes the dehydrogenation of unsaturated alcohols over a copper catalyst having a specific surface area of 0.01 to 1.5 m$^2$/g at 150 to 300° C. essentially in the absence of oxygen. When α,β-unsaturated alcohols are used as starting materials, β,γ-unsaturated aldehydes and saturated aldehydes are formed as by-products; the selectivity for α,β-unsaturated aldehydes is low (cf. page 2, last paragraph). Such mixtures have to be separated into their components in costly separating operations.

DE-B-20 20 865 and DE-B-20 41 976 describe the dehydrogenation of β,γ-unsaturated alcohols and of α,β-unsaturated alcohols, respectively, to form α,β-unsaturated aldehydes. The dehydrogenation catalysts mentioned include mixed catalysts, for example mixed catalysts composed of copper and silver. It is disadvantageous, however, that appreciable amounts of nucleophilic substances have to be added. When 3-methyl-3-buten-1-ol is used as starting material, good results are obtained only at incomplete conversion, which, according to DE-B-22 43 810, leads to problems with the removal of the unconverted starting material.

Dehydrogenation of isoprenol over metallic copper without oxygen by the process of DE-B-25 17 859 gives rise to appreciable amounts of isovaleraldehyde and the activity of the catalysts drops off rapidly within a few days, necessitating frequent regeneration.

FR-A-2 231 650 describes the preparation of aldehydes and ketones from the corresponding alcohols by air oxidation at 250 to 600° C. in the presence of a gold catalyst. The advantage of the gold catalyst resides in the higher selectivity compared with copper and silver catalysts, reducing by-product formation. The disadvantage of this process is the high catalyst expense, since an unsupported gold catalyst is used.

DE-B-27 15 209 and EP-B-55 354 describe the oxidative dehydrogenation of 3-alkylbuten-1-ols over catalysts consisting of layers of silver and/or copper crystals in the presence of molecular oxygen. The oxygen quantities range from 0.3 to 0.7 mol, based on the feedstock. The disadvantage with this process is that catalyst expenses are high owing to the use of unsupported silver and good selectivities can be achieved only if defined catalyst particle sizes or particle size distribution are used in a layer construction, at times even specific mixtures of layers of copper and silver crystals. This entails not only costly packing of the reactor but also costly catalyst recovery. In addition, the high reaction temperatures employed give rise to sintering of the metal crystals, which leads to pressure buildup and short onstream times.

JP-A-60/246340 describes the gas phase oxidation of prenol to prenal at 300 to 600° C. in the presence of oxygen and a supported catalyst. The supported catalyst has to be prepared in a complicated manner by impregnating the support with aqueous solutions of AgNO$_2$, Cu(NO$_3$)$_2$×3H$_2$O and Mg(NO$_3$)$_2$×6H$_2$O, drying, calcination within a specific temperature range and activation under hydrogen. The catalyst does provide good selectivity at 96.6%, but only at the cost of low conversion, so that it is hardly suitable for industrial purposes.

JP-A-58/059 933 describes the production of aldehydes and ketones by oxidative dehydrogenation of alcohols in the presence of a silver catalyst which additionally includes phosphorus. To maintain the selectivity of the reaction, a phosphorus compound is additionally introduced into the alcohol stream, making contamination of the product likely. In view of the intended use of the aldehydes for scents and vitamins, the addition of an organophosphorus compound is obviously disadvantageous.

According to EP 244 632 B1, even unsaturated aliphatic alcohols are advantageously convertible into the corresponding aldehydes by continuous oxidative hydrogenation if the reaction is carried out in the gas phase at 300 to 600° C. over a suitable catalyst disposed in short and thin reaction tubes which are arranged between tubesheets and which are surrounded by a fluidic heat transfer medium flowing in the lateral direction.

A very advantageous embodiment of the process of EP 244 632 comprises contacting the vaporous gas mixture emerging from the tube bundle reactor at −20 to +50° C. with water and/or a condensed reaction mixture comprising water and unconverted alcohols shortly after the vaporous gas mixture emerging from the tube bundle reactor has been in contact with the catalyst, removing the aldehydes from the resulting condensate as described in EP 55 354 A1 and recycling the unconverted alcohols into the process.

The disadvantage with this otherwise very advantageous process is that, despite frequent burnoff of coke and other deposits on the catalyst, both the conversion and the selectivity will drop off sharply after some weeks into a continuous run (see Comparative Example), so that the catalyst has to be changed. When such a reactor is opened, the reaction tubes are found to be totally plugged for the most part. The plugs in the individual tubes are so hard that the tubes in question have to be drilled out with a hammerdrill, which is very time-consuming and can lead to tube damage. The gradual plugging of the individual tubes cannot be prevented either by upstream disposition of an arranged packing of metal fabric (Sulzer BX) as a prefilter or by overcoating of the catalyst layer with inert particles, such as glass and porcelain balls, as a filter.

A further disadvantage of this process is that it is difficult to fabricate tube bundle reactors having very short reaction tubes to achieve high capacities, ie. where a very large number of reaction tubes are required.

SUMMARY OF THE INVENTION

It is an object of the present invention to improve the above-described process of EP 244 632 B1 (incorporated herein by reference) for continuous industrial production of unsaturated aliphatic aldehydes by oxidative dehydrogenation of the corresponding alcohols with an oxygen-comprising gas over a supported catalyst consisting of copper, silver and/or gold on an inert support in a tube bundle reactor, rapid cooling of the reaction gases and removal of the aldehydes from the resulting condensate to the effect that the prior art disadvantages no longer arise, ie. that the continuous process can be operated for long periods, ideally for periods extending over several years, without shutdown of the plant and without costly drilling out of the reaction tubes in a readily manufacturable reactor.

SUMMARY OF THE INVENTION AND PREFERRED EMBODIMENTS THEREOF

Figure 1A:
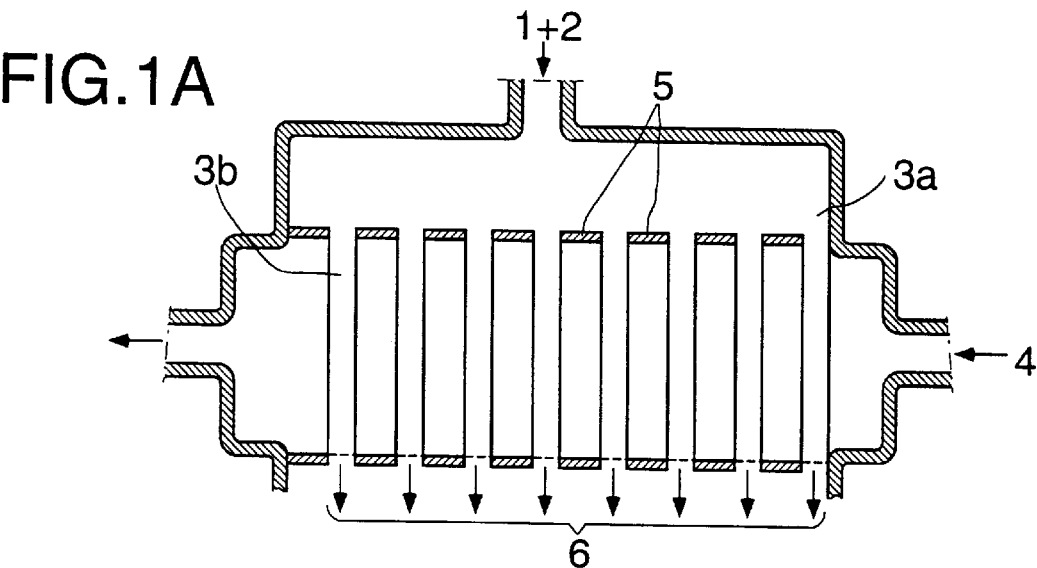
FIGS. 1A, 1B, 1C illustrate various embodiments of the invention.

We have found that this object is achieved by a process for continuous production of unsaturated aliphatic aldehydes of the general formula I

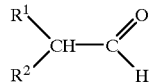

where (isoprenal) $R^1$ is hydrogen and $R^2$ is

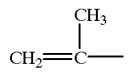

or where (prenal) $R^1$ and $R^2$ are together

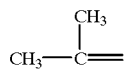

by oxidative dehydrogenation of either of the two or a mixture of the two 3-alkylbuten-1-ols of the general formula II (II)

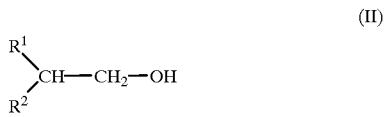

(prenol and/or isoprenol) with an oxygen-comprising gas over a supported catalyst consisting of copper, silver and/or gold on an inert support in a tube bundle reactor, rapid cooling of the reaction gases and removal of the aldehydes from the resulting condensate, which comprises a) vaporizing the vapor of either or both of the 3-alkylbuten-1-ols of the general formula II, b) admixing the alcohol vapor (1) with an oxygen-comprising gas (2), c) initially passing the resulting oxygen-comprising alcohol (1+2) at above the dew point of the alcohol but below the commencement temperature of the reaction through a layer at least 0.5 cm in thickness, preferably a layer (3a) from 0.6 to 5 cm in thickness, of one of the abovementioned supported catalysts, which preferably occupies the cross section of the entire reactor, and only then d) reacting the oxygen-comprising alcohol vapor at from 300 to 600° C. in a sufficient number, for the desired capacity, of parallel reaction tubes (3b) surrounded by a fluidic heat transfer medium (4), packed with one of the supported catalysts mentioned and having an internal diameter D or from about 0.5 to 3 cm, preferably from 1 to 2 cm, and a length of at least 5 cm, preferably within the range from 35 to 60 cm, to form the corresponding aldehyde.

Figure 1B:
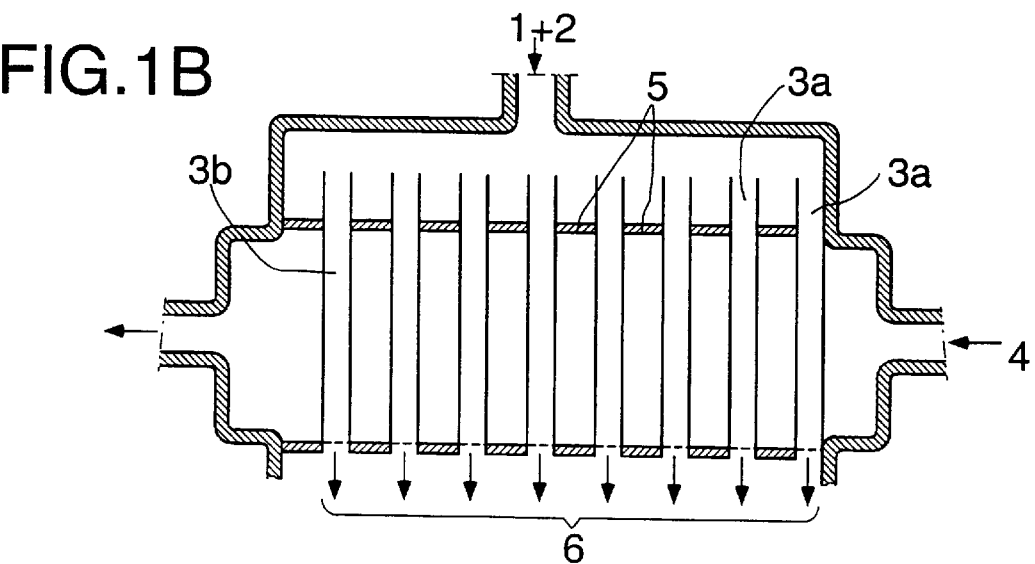
Figure 1C:
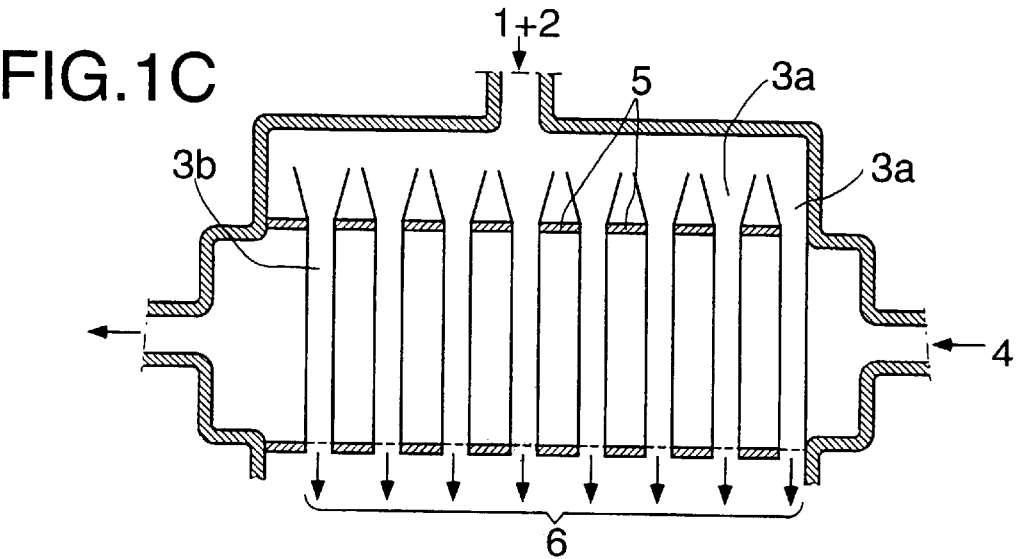

Three advantageous embodiments of the process are diagrammatically illustrated in FIGS. 1a, 1b and 1c, where 1 is the alcohol vapor, 2 is the oxygen-comprising gas, 3a is the layer of a supported catalyst which is at least 0.5 cm in thickness and preferably occupies the cross section of the entire reactor (FIG. 1a), 3b denotes the reaction tubes packed with a supported catalyst and surrounded by a fluidic heat transfer medium, 4 is the fluidic heat transfer medium, 5 is the tubesheet and 6 is the vaporous reaction mixture comprising the resulting aldehyde and unconverted alcohol.

In an advantageous embodiment of the process according to the invention, the supported catalyst used is a support catalyst consisting of metallic silver on an inert support.

In a very convenient embodiment, reaction steps c) and d) are carried out with the same supported silver catalyst and the catalysts of reaction steps c) and d) are in direct contact.

In a particularly advantageous embodiment of the process according to the invention, reaction steps c) and d) are carried out with a supported silver catalyst which consists of spheres of an inert support material which have been coated with from 0.1 to 20% by weight, based on the amount of the support, of a layer of metallic silver in the form of a smooth, attrition-resistant shell, the largest diameter d) of the coated supported catalyst spheres being subject to a relation with the internal diameter D of the reaction tubes of d/D= 0.05–0.3, preferably 0.1–0.2.

As Inventive Example 1 reveals, application of the measures according to the invention made it possible to use the tube bundle reactor for the continuous industrial production of prenal for more than 3 years without loss of capacity and without change of catalyst.

There is no need for costly drilling of the reaction tubes to clean them out; the catalyst can simply be removed by means of a vacuum cleaner. It is very surprising that such simple measures produce such an advantageous effect.

A further advantage of the process according to the invention is that the reactor can be operated to a higher space velocity.

It is characteristic of the preparation of aldehydes by catalytic oxidation of alcohols over silver catalysts that the selectivity decreases with increasing conversion. U.S. Pat. No. 4,097,535 discloses that, for example, in the oxidation of octanol over silver catalysts, the conversion can be increased from 77% to 91% without decrease in the selectivity by passing the mixture of the alcohol and the oxygen-comprising gas initially through a prereactor zone comprising supported silver catalyst and only then into the reactor zone at 300 to 600° C., but the Examples clearly show that the objective of increasing the conversion can understandly only be achieved if the prereactor zone, which is heated by external sources of heat, is at temperatures above the commencement temperature of the reaction.

By contrast, the temperatures in the layer of the supported catalyst of step c) of the process according to the invention are below the commencement temperature of the reaction. The conversion is accordingly not greater than without application of the measures according to the invention. The continuous industrial process operates with advantage at conversions from 50 to 60% and with recycling of the unconverted alcohol. Presumably, the extreme blockages in the reaction tubes are due to very small quantities of by-products in the starting alcohol supplemented by recycling of unconverted alcohol. Surprisingly, these catalyst-destroying reactions are avoided when the oxygen-comprising alcohol vapor is initially passed through a suitable supported catalyst, preferably a supported silver catalyst, especially the same supported silver catalyst as in reaction step d), at temperatures below the commencement temperature. A particularly advantageous embodiment of the product of prenal comprises simply mixing the vaporizer alcohol vapor with hot air at from 140 to 160° C. and passing the resulting hot alcohol/air mixture at from 120 to 130° C. into the otherwise unheated supported catalyst layer of process step c).

The thickness of this catalyst layer depends on the reactor design on the one hand and on the diameter of the catalyst particles on the other. In general, a somewhat thicker layer is required in the case of comparatively large reactors to ensure that individual reaction tubes are not insufficiently protected and become blocked as a result. The layer, on the other hand, has to have at least the thickness of 2 times the catalyst particle diameter. This results in layer thicknesses of at least 0.5 cm, preferably from 0.6 to 5 cm, especially from 1 to 3 cm.

It has surprisingly been found that application of reaction step c) according to the invention makes it possible to use in the tube bundle reactor even reaction tubes which are longer than the relatively short tubes described in EP 244 632, which is beneficial not only with regard to the construction of the reactors but also with regard to the catalyst on-stream time.

Suitable supported catalysts for the process of the invention are particles comprising metallic copper, silver and/or gold, preferably silver, on an inert support material.

If desired, the catalyst may also be diluted with an inert material not coated with active composition. Suitable inert materials, which are also useful as support material, include ceramic materials, such as aluminum oxide, silicon dioxide, magnesium oxide, silicon carbide and especially steatite. A catalyst layer, however, should comprise not less than 10% of active-material particles.

Suitable inert shapes for the catalyst include primarily spheres but also other bodies such as ellipsoids, cylinders or rings. The diameter d of the spheres, or the largest diameter of the other bodies, may be within the range from 0.1 to 1.5 cm diameter, the diameters depending on the internal diameter of the tube bundle tubes.

The catalyst particles are, for example, dumped onto a silver or stainless steel mesh in the customarily upright reactor.

The active catalyst metal is preferably applied to the inert material by flame spraying, but other methods, for example impregnation or plasma spraying, are also suitable, as long as the result is an attrition-resistant shell which, otherwise, should be as smooth as possible.

The catalyst is simple to prepare and is simple to introduce into the reactor especially in the case of spheres. A further advantage of the regular shape of the catalyst is that, without further measures, orderly close packing is obtained in the reactor and, in the case of tube bundle reactors, each individual tube of the bundle exhibits a very similar pressure drop owing to the uniformity of packing. The identical pressure drop arising in many tubes of a tuba bundle reactor leads to equal flow through the individual pipes and thereby evidently to a significant improvement in the selectivity of the reaction. Individual pipes do not experience higher space velocities, so that the on-stream time of the catalyst under the conditions of the invention is very high, a number of years in practice.

The oxidizing agent used may be not only pure oxygen but also gases comprising free oxygen, especially air. The oxygen and the alcohol are advantageously employed in a molar ratio of from 0.1 to 0.8, especially of from 0.2 to 0.4, mol of oxygen per mole of alcohol.

Depending on the desired reactor capacity, the tube bundle reactor used has from 100 to 10,000 tubes at least 5, preferably from 10 to 60, cm, especially from 35 to 60 cm, in length. For experimental purposes, it is sufficient to use one tube.

The reaction is generally carried out at a pressure within the range from 0.8 to 2 bar, preferably at atmospheric pressure, in a continuous manner.

The catalyst is advantageously subjected to a space velocity of from 0.5 to 7 t, especially from 1 to 5 t, of alcohol per $m^2$ of catalyst cross-section per hour.

The reaction mixture is worked up in a conventional manner. For example, the hot reaction gases are absorbed with a solvent such as water or preferably in condensed product mixture directly on emergence from the reactor.

The residence time of the gas mixture in the reaction tube is within the range from 0.0005 to 1, preferably within the range from 0.001 to 0.05, seconds.

Suitable starting compounds are the methylbutenols of the general formula II

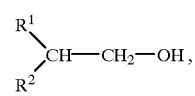

II where $R^1$ and $R^2$ are each as defined above. Methylbutenols are known compounds and obtainable by known methods.

To produce prenal, a particularly preferred embodiment of the process of the invention comprises a) vaporizing prenol and/or isoprenol, b) admixing the prenol and/or isoprenol vapor with an oxygen-comprising gas, c) passing the resulting oxygen-comprising vapor of prenol and/or isoprenol at just above the dew point through a layer of a supported silver catalyst which is from 0.5 to 4 cm in thickness and which preferably occupies the cross section of the entire reactor, then d) reacting the oxygen-comprising vapor of prenol and/or isoprenol in a sufficient number, for the desired capacity, of reaction tubes which are packed with a supported silver catalyst and have an internal diameter of from 1 to 2 cm and a length of from 35 to 60 cm to form a mixture of prenal and isoprenal, and e) isomerizing the isoprenal present in the resulting mixture of prenal and isoprenal into prenal in a conventional manner.

The process of the invention makes it possible to produce the α,β-unsaturated aldehydes, especially prenal, which are sought after as intermediates for the synthesis of scents, vitamins and carotenoids in good yields in advantageously fabricable tube bundle reactors with catalyst on-stream times of several years.

INVENTIVE EXAMPLE 1

Figure 2:
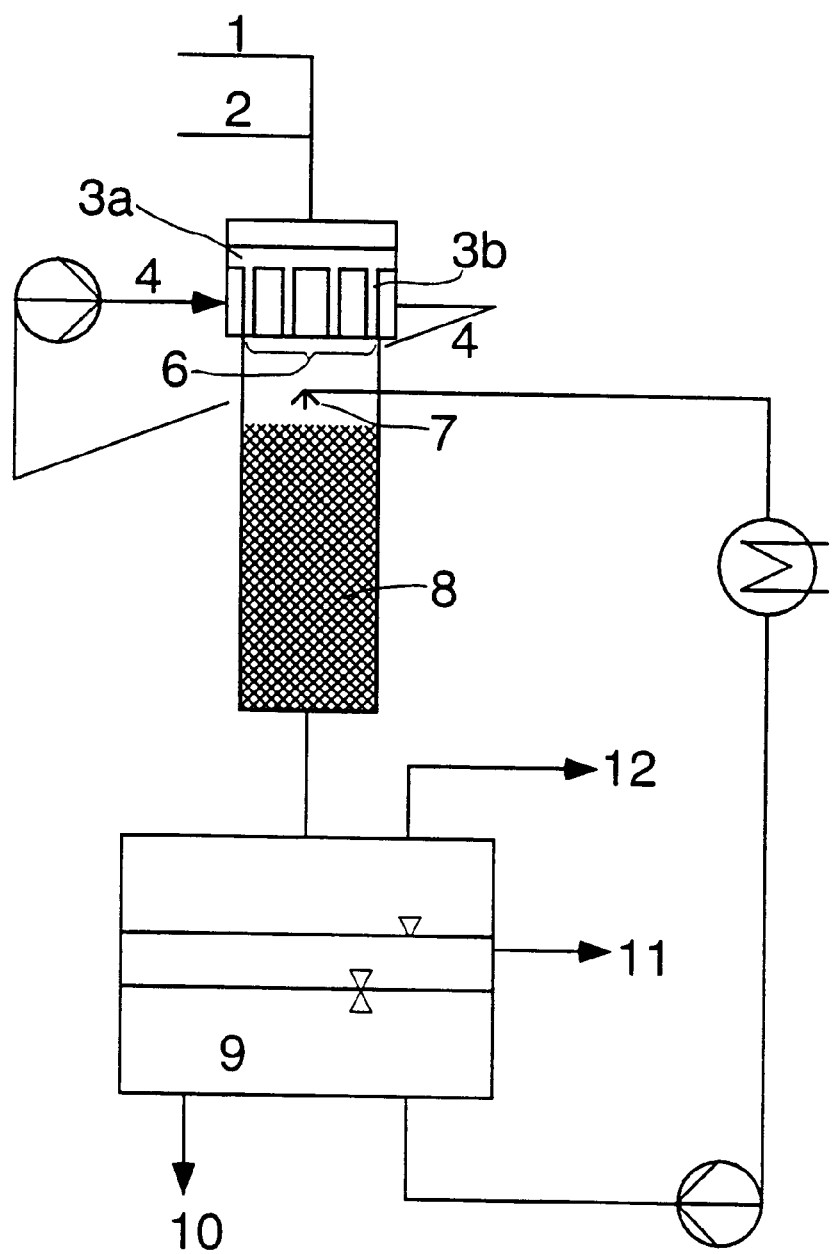
FIG. 2 diagrammatically illustrates an industrial plant according to the invention.

An industrial plant as diagrammatically depicted in FIG. 2 was used.

Crude alcohol comprising from about 70 to 80% by weight of isoprenol was vaporized and the vapor (1) was mixed in a mixing zone with air (2) heated to 140–160° C. and this hot mixture, having a temperature of from 125 to 130° C., was passed initially through the supported silver catalyst layer (3a) disposed on the tubesheet and then into the reactor tube (3b) packed with the supported silver catalyst and surrounded by a flow of hot salt melt (4) at about 360° C. used for commencing the reaction and for removing the heat of reaction. The silver catalyst used consisted of the same stalactite balls coated with metallic silver as will be described in the Comparative Example.

The hot reaction gases (6) obtained in the reaction were cooled down in a quench (7) with downstream column (8), said quench (7) being supplied with the aqueous phase (9) of the product effluent. The two liquid phases of the reactor effluent were removed via lines (11) and (10) for workup and for the quench, respectively; gaseous fractions were disposed of via line (12).

The above-described industrial reactor was operated at a teed within the range from 120 g to 360 g of crude alcohol for 1167 days without change of catalyst.

During the run, operation was interrupted for a few hours once a week to burn coke and other organic products off the catalyst.

On day 1165 a mass balance run was carried out similarly to Comparative Example 1a. The reactor was fed with 127° C. mixture of 350.6 g of crude alcohol vapor comprising 74.2% of 3-methyl-3-buten-1-ol and 50.9 l (S.T.P.) air per hour (h) per reaction tube. The postisomerization reactor effluent was found to contain 122.0 g of 3-methyl-2-buten-1-al and 137.0 g of 3-methyl-3-buten-1-ol, which corresponds to a conversion of 52.1% and a selectivity of 91.2%.

INVENTIVE EXAMPLE 2

In the industrial plant diagrammatically depicted in FIG. 2 and more particularly described in Inventive Example 1, 240.2 g of crude alcohol (1) (comprising 64.0% by weight of 3-methyl-3-buten-1-ol and 12.5% by weight of 3-methyl-2-buten-1-ol) were vaporized per h per reaction tube and mixed with 37.1 l (S.T.P.) of hot air (2) per h per reaction tube. The vapor/air mixture was passed at 125° C. initially through the supported silver catalyst layer (3a) disposed on the tubesheet and then into the reaction tubes packed with the same silver catalyst and surrounded by flow of salt melt (4) used for commencing the reaction and for removing heat.

The supported silver catalyst used consisted of the same stalactite balls coated with metallic silver as are described in the Comparative Example.

Isomerization of the crude effluent yielded 88.1 l of 3-methyl-2-buten-1-al, 53.7 g of 3-methyl-3-buten-1-ol and 10.5 g of 3-methyl-2-buten-1-ol.

The conversion based on the two alcohols was 54.3% and the selectivity 90.4%.

INVENTIVE EXAMPLE 3

Verification of the action of a supported silver catalyst at 250° C. with regard to the formation of 3-methyl-2-buten-1-al This experiment was carried out using a laboratory apparatus featuring a tube having an internal diameter of 12 mm and a length of 400 mm.

The reaction tube was fed with a 130° C. mixture of the vapor of 90 g of pure 3-methyl-3-buten-1ol and air (weight ratio of 3-methyl-3-buten-1-ol to air=1:0.3), and the supported silver catalyst in the reaction tube was adjusted to a temperature of 250° C. The reactor effluent was found to contain no prenal, ie. the conversion was 0%.

This Example shows that 250° C., and hence the maximum temperature which might arise in the supported silver catalyst layer on the tubesheet, is not high enough to bring about a conversion to prenal.

Comparative Example

Production of 3-methyl-2-buten-1-al

Figure 3:
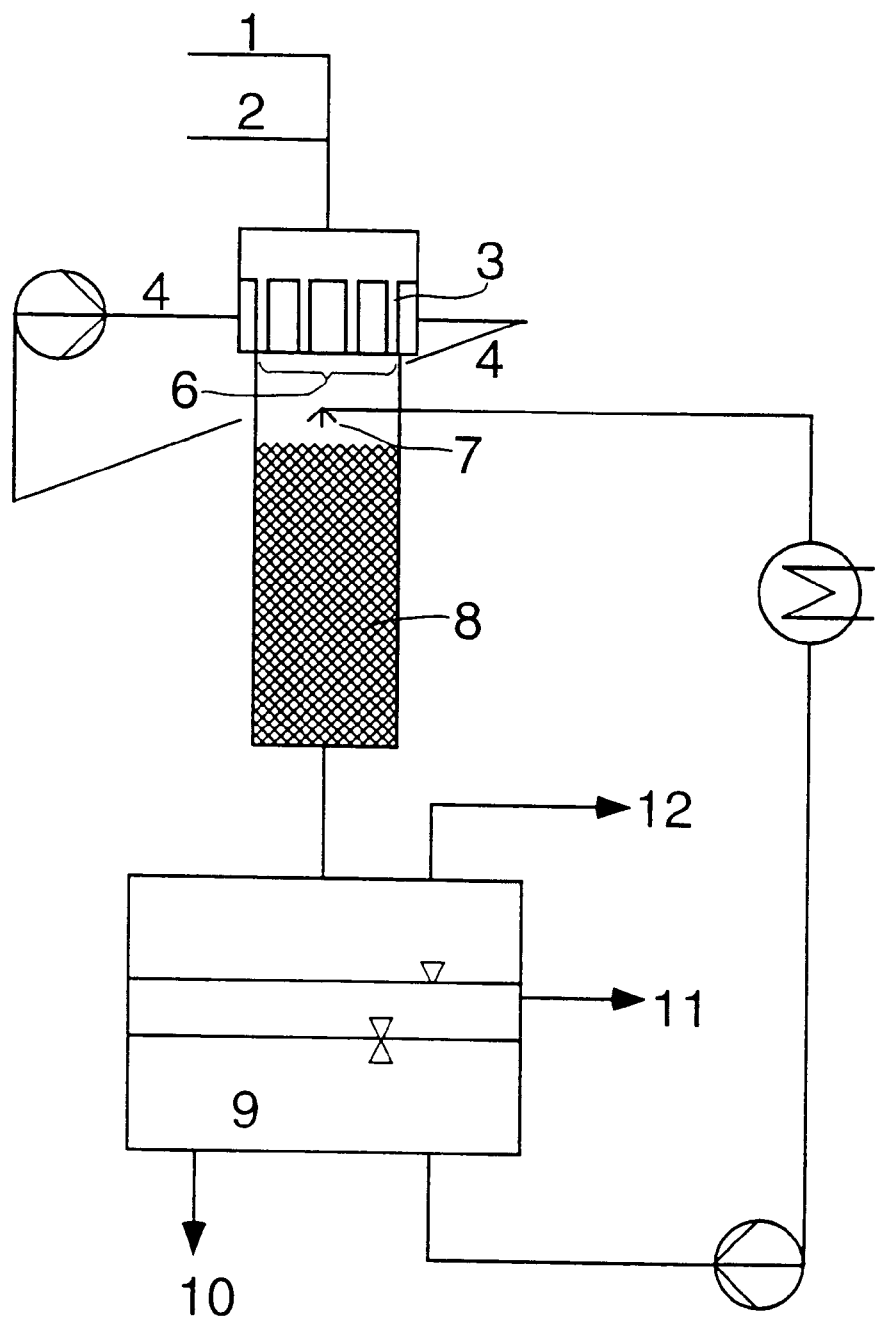
FIG. 3 diagrammatically illustrates an industrial plant according to the prior art.

An industrial plant as diagrammatically depicted in FIG. 3 was used.

A mixture of prenol and isoprenol was vaporized, the vapor (1) was mixed in a mixing zone with the hot air (2), and this mixture was passed into the tube bundle reactor tubes (3) packed with a silver catalyst. The catalyst consisted of an attrition-resistant layer of about 4% by weight of metallic silver on stalactite balls from 0.2 to 0.25 cm in diameter. The reactor tubes were surrounded by a flow of salt melt (4) to commence the reaction and to remove heat.

The combined hot reaction gases (6) obtained in the reaction were cooled down in a quench (7) with downstream column (8), said quench (7) being supplied with the aqueous phase (9) of the product effluent. The two liquid phases of the reactor effluent were removed via lines (11) and (10) for workup and for the quench, respectively; gaseous fractions were disposed of via line (12).

a) The reactor was fed with a 126° C. mixture of 248 g of crude alcohol vapor and 34.4 l (S.T.P.) of air per hour per reaction tube (12 mm ⌀).

The 3-methyl-3-buten-1-ol content of the crude alcohol was 71.43%. The temperature of the salt melt surrounding the tubes was maintained at 360° C.

The postisomerization quench effluent contained 82.6 g of prenal (3-methyl-2-buten-1-al) and 85.1 g of unconverted alcohol, which corresponds to a conversion of 52% and a selectivity of 91.8% of theory.

b) The industrial reactor was fed with a mixture of 354.7 g of crude alcohol vapor having a 3-methyl-3-buten-1-ol content of 71.43% and 69.6 l (S.T.P.) of air per hour per individual tube.

The alcohol/air mixture had a temperature of 130° C. The salt bath temperature was maintained at 360° C.

The postisomerization crude effluent contained 165.2 g of 3-methyl-2-buten-1-al and 167.5 g of 3-methyl-3-buten-1-ol, which corresponds to a conversion of 52.8% and a selectivity of 90.4% of theory.

c) The above-described reactor was operated with a mixture of starting-material vapor and air as described above under a) and b) for 95 days. During this period, the operation was interrupted for several hours once a week to burn coke and other organic products off the catalyst. After 95 days in each case, conversion and selectivity decreased sharply. The feed per reaction tube had to be reduced to 49 g of crude alcohol.

The postisomerization quench effluent contained 8.9 g of 3-methyl-2-buten-1-al and 21 g of 3-methyl-3-buten-1-ol, which corresponds to a conversion of only 40% and a selectivity of only 65% of theory.

We claim:

1. In a process for continuous industrial production of aldehydes

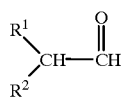
(I)

where (isoprenal) $R^1$ is hydrogen and $R^2$ is

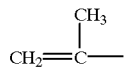

by oxidative dehydrogenation of the corresponding alcohols with an oxygen-comprising gas over a supported catalyst consisting of copper, silver and/or gold on an inert support in a tube bundle reactor, rapid cooling of the reaction gases and removal of the aldehydes from the resulting condensate while recycling the unconverted alcohols, which comprises a) vaporizing 3-alkylbuten-1-ols of the general formula II

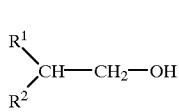
(II)

b) admixing the alcohol vapor with an oxygen-comprising gas, c) the improvement comprising initially passing the resulting oxygen-comprising alcohol vapor at above the dew point of the alcohol but below the commencement temperature of the reaction through a layer of one of the abovementioned supported catalysts which is at least 0.5 cm in thickness and only then d) reacting the oxygen-comprising alcohol vapor at from 300 to 600° C. in parallel reaction tubes surrounded by a fluidic-heat transfer medium, packed with the supported catalyst and having an internal diameter D of from about 0.5 to 3 cm and a length of at least 5 cm, to form the corresponding aldehyde.

2. A process as claimed in claim 1, wherein the supported catalyst used is a supported catalyst consisting of metallic silver on an inert support.

3. A process as claimed in claim 1, wherein the supported catalysts of reaction steps c) and d) are in direct contact.

4. A process as claimed in claim 1, wherein reaction steps c) and d) are carried out with the same supported silver catalyst and the catalysts of reaction steps c) and d) are in direct contact.

5. A process as claimed in claim 1, wherein reaction steps c) and d) are carried out with a supported silver catalyst which consists of spheres of an inert support material which have been coated with from 0.1 to 20% by weight, based on the amount of the support, of a layer of metallic silver in the form of a smooth, attrition-resistant shell, the largest diameter d) of the coated supported catalyst spheres being subject to a relation with the internal diameter D of the reaction tubes of d/D=0.05–0.3.

6. A process as claimed in claim 1, wherein the layer of reaction step c) which is at least 0.5 cm in thickness occupies the cross section of the entire reactor.

7. A process as claimed in claim 1, wherein the layer of reaction step c) through which the oxygen-comprising alcohol vapor is passed initially is a layer of a supported silver catalyst from 0.6 to 5 cm in thickness.

8. A process as claimed in claim 1, wherein the reaction of the oxygen-comprising alcohol vapor in reaction step d) to form the corresponding aldehyde is carried out in a multiplicity of reaction tubes having an internal diameter of from 1 to 2 cm and a length of from 35 to 60 cm.

9. A process as claimed in claim 1, wherein 3-methyl-2-buten-1-al is prepared by a) vaporizing 3-methyl-2-buten-1-ol and/or 3-methyl-3-buten-1-ol, b) admixing the 3-methyl-2-buten-1-ol and/or 3-methyl-3-buten-1-ol vapor with an oxygen-comprising gas, c) passing the resulting oxygen-comprising vapor of 3-methyl-2-buten-1-ol and/or 3-methyl-3-buten-1-ol at just above the dew point through a layer of a supported silver catalyst which is from 0.5 to 4 cm in thickness, d) reacting the oxygen-comprising vapor of 3-methyl-2-buten-1-ol and/or 3-methyl-3-buten--1-ol in reaction tubes which are packed with a supported silver catalyst and have an internal diameter of from 1 to 2 cm and a length of from 35 to 60 cm to form a mixture of 3-methyl-2-buten-1-al and 3-methyl-3-buten-1-al, and e) isomerizing 3-methyl-3-buten-1-al present in the resulting mixture into 3-methyl-2-buten-1-al in a conventional manner.

10. A process as claimed in claim 5, wherein the internal diameter D is 0.1–0.2.

* * * * *